United States Patent
Moon et al.

(10) Patent No.: US 12,329,798 B2
(45) Date of Patent: Jun. 17, 2025

(54) COMPOSITION FOR PREVENTING OR TREATING HYPERTENSION

(71) Applicant: Hobin Moon, Seoul (KR)

(72) Inventors: Hobin Moon, Seoul (KR); Doo Suk Lee, Gyeonggi-do (KR); Wonwoo Lee, Seoul (KR); Seunghwan Son, Seoul (KR)

(73) Assignee: Hobin Moon, Seoul (KR)

( * ) Notice: Subject to any disclaimer, the term of this patent is extended or adjusted under 35 U.S.C. 154(b) by 452 days.

(21) Appl. No.: 17/779,680

(22) PCT Filed: Nov. 27, 2020

(86) PCT No.: PCT/KR2020/017187
§ 371 (c)(1),
(2) Date: May 25, 2022

(87) PCT Pub. No.: WO2021/107719
PCT Pub. Date: Jun. 3, 2021

(65) Prior Publication Data
US 2022/0401503 A1 Dec. 22, 2022

(30) Foreign Application Priority Data
Nov. 29, 2019 (KR) ........................ 10-2019-0157657

(51) Int. Cl.
| | |
|---|---|
| *A61K 36/488* | (2006.01) |
| *A61K 36/346* | (2006.01) |
| *A61K 36/79* | (2006.01) |
| *A61K 36/8945* | (2006.01) |
| *A61K 36/8968* | (2006.01) |
| *A61K 36/8994* | (2006.01) |
| *A61P 9/12* | (2006.01) |

(52) U.S. Cl.
CPC .......... *A61K 36/488* (2013.01); *A61K 36/346* (2013.01); *A61K 36/79* (2013.01); *A61K 36/8945* (2013.01); *A61K 36/8968* (2013.01); *A61K 36/8994* (2013.01); *A61P 9/12* (2018.01); *A61K 2236/331* (2013.01); *A61K 2236/333* (2013.01)

(58) Field of Classification Search
None
See application file for complete search history.

(56) References Cited

FOREIGN PATENT DOCUMENTS

| | | | | |
|---|---|---|---|---|
| CN | 104147549 A | | 11/2014 | |
| CN | 105535005 A | * | 5/2016 | |
| CN | 105524138 B | * | 12/2018 | ............... C07K 7/06 |
| KR | 10-1996-0000237 A | | 1/1996 | |
| KR | 10-2004-0023196 A | | 3/2004 | |
| KR | 10-2005-0121815 A | | 12/2005 | |
| KR | 10-0572621 B1 | | 4/2006 | |

OTHER PUBLICATIONS

Cai et al. (Antihypertensive effect of total flavone extracts from Puerariae Radix, Journal of Ethnopharmacology 133 (2011) 177-183). (Year: 2011).*
KR20040082563A translated doc (Year: 2004).*
Cai et. al (Antihypertensive effect of total flavone extracts from Puerariae Radix, Journal of Ethnopharmacology, vol. 133, Issue 1, Jan. 7, 2011, p. 177-183) (Year: 2011).*
Amat et. al. (Aqueous extract of dioscorea opposite thumb. Normalizes the hypertension in 2K1C hypertensive rats, BMC Complementary and Alternative Medicine 14, article No. 36 (2014) (Year: 2014).*
Chun et. al. (The protective effects of Schisandra chinensis fruit extract and its lignans against cardiovascular disease: A review of the molecular mechanisms, Fitoterapia 97 (2014) 224-233) (Year: 2014).*
The Ortho Phosphorous Orient Medical Hospital website posted writing, and "The ortho phosphorous sensuousness tang" (Aug. 21, 2018) <web.archive.org/web/20180821084834/http://www.jungindiet.com/jmi.php>.
Office Action from corresponding Korean Application No. 10-2019-0157657, Dated Aug. 8, 2023.
International Search Report from corresponding PCT Application No. PCT/KR2020/017187, dated Mar. 22, 2021.
Fang Qicheng, "Some current study and research approaches relating to the use of plants in the traditional Chinese medicine", Journal of Ethnopharmacology, vol. 2, pp. 57-63.
Korean Office Action Corresponding to Korean Application No. 10-2019-0157657. dated Dec. 20, 2023.

* cited by examiner

Primary Examiner — Terry A McKelvey
Assistant Examiner — Jacob A Boeckelman
(74) Attorney, Agent, or Firm — Harness, Dickey & Pierce, P.L.C.

(57) ABSTRACT

The present invention relates to a composition for preventing or treating hypertension, the composition comprising, as an active ingredient, a complex extract of Puerariae Radix, Platycodonis Radix, Liriopis Tuber, Dioscoreae Rhizoma, Coicis Semen, and Schisandrae Fructus. A pharmaceutical composition or food composition according to the present invention can be used to effectively prevent, ameliorate, or treat hypertension or hypertension-related diseases.

5 Claims, 2 Drawing Sheets

COMPOSITION FOR PREVENTING OR TREATING HYPERTENSION

CROSS-REFERENCE TO RELATED APPLICATIONS

This application is a national phase application of PCT Application No. PCT/KR2020/017187, filed on Nov. 27, 2020, which claims the benefit and priority to Korean Patent Application No. 10-2019-0157657, filed on Nov. 29, 2019. The entire disclosures of the applications identified in this paragraph are incorporated herein by references.

TECHNICAL FIELD

The present disclosure was made with the support of the Ministry of Health and Welfare, Republic of Korea, under Project No. H116C0275, which was executed under the research project named "Research of Saengmaeksangagambang for development of herbal medicine preparations for treating menopausal disorders" in the research business titled "Development of standard clinical guidance for Korean Medicine (Research of industrialization of projects designed to make Korean Medicine treatment technologies as public resources)", by Helixmith Co., Ltd., under the management of the Korea Health Industry Development Institute, from 28 May 2019 to 30 Nov. 2019.

The present disclosure relates to a composition for preventing or treating hypertension, the composition comprising, as an active ingredient, a complex extract of Puerariae Radix, Platycodonis Radix, Liriopis Tuber, Dioscoreae Rhizoma, Coicis Semen, and Schisandrae Fructus.

BACKGROUND ART

Blood pressure is the pressure of blood against the walls of the arteries. Blood pressure is highest when the heart contracts and pumps blood to the arteries, and this is called the systolic pressure. Blood pressure is lowest when the heart expands and receives blood, and this is called the diastolic pressure. The elevation in the blood pressure due to various reasons is called hypertension. Hypertension is known as one of the greatest risk factors in the occurrence of diseases in the world, and about 30% of the Korean adult population is assumed to have hypertension. On the systolic blood pressure of 110-115 mmHg and the diastolic blood pressure of 70-75 mmHg as the lowest basis, a more elevated blood pressure increases the risk and mortality of cardiovascular disease, chronic kidney disease, and retinopathy. The mortality of cardiovascular disease according to the blood pressure continuously doubles for each increase of 20 mmHg for the systolic blood pressure and 10 mmHg for the diastolic blood pressure from 115/75 mmHg. According to a 6-year follow-up study of male public servants and private school staffs (Korean Medical Insurance Corporation study, KMIC) as domestic data, hypertensive patients with a blood pressure of 140/90 mmHg or higher had a 2.6-fold higher risk of cardiovascular disease compared with persons with a blood pressure of lower than 130/85 mmHg. Hypertension is one of the most important risk factors for stroke, and based on a blood pressure of less than 130/85 mmHg, the risk of coronary artery disease was 2.51-fold higher for a blood pressure of 130-140/85-90 mmHg and 5.08-fold higher for a high blood pressure of 180/110 mmHg or higher. According to the results of most hypertension clinical studies, a decrease in systolic blood pressure of 10-20 mmHg and a decrease in diastolic blood pressure of 5-10 mmHg reduce the risk of stroke by 30-40% and ischemic heart disease by 15-20%. Therefore, hypertension has a very high risk of hypertension itself as well as hypertension-related diseases. Types of hypertension are divided into essential hypertension of unknown causes and secondary hypertension caused by causative diseases, and at least 80% of hypertension cases are known to belong to essential hypertension.

Many antihypertensive drugs for the treatment of hypertension have been currently developed and used, and are classified into, depending on the mechanism of action and the action site, diuretics, sympathetic nervous system-acting drugs (α2-adrenergic antagonists and β-adrenergic antagonists), vasodilators, calcium channel blockers, angiotensin converting enzyme (ACE) inhibitors, and the like. However, functional foods or drugs for preventing, treating, or alleviating hypertension, containing herbal medicinal ingredients extracted from natural substances, have not yet been available on the market.

SUMMARY

Technical Problem

The present inventors conducted intensive research to develop a natural substance-derived composition capable of preventing, treating, or alleviating hypertension. As a result, the present inventors established that a composition comrising a complex extract of Puerariae Radix, Platycodonis Radix, Liriopis Tuber, Dioscoreae Rhizoma, Coicis Semen, and Schisandrae Fructus had superb effects in preventing, treating, or alleviating hypertension, and thus completed the present disclosure.

Accordingly, an aspect of the present disclosure is to provide a pharmaceutical composition, comprising a complex herbal medicine extract, for preventing or treating hypertension.

Another aspect of the present disclosure is to provide a food composition, comprising a complex herbal medicine extract, for preventing or alleviating hypertension.

Still another aspect of the present disclosure is to provide a method for preventing, treating, or alleviating hypertension, the method comprising administering the composition to a subject.

Solution to Problem

The present inventors conducted intensive research to develop a natural substance-derived substance capable of preventing, treating, or alleviating hypertension. As a result, the present inventors established that a composition comprising a complex extract of Puerariae Radix, Platycodonis Radix, Liriopis Tuber, Dioscoreae Rhizoma, Coicis Semen, and Schisandrae Fructus had superb effects in preventing, treating, or alleviating hypertension.

In accordance with an aspect of the present disclosure, there is provided a pharmaceutical composition for preventing or treating hypertension or a hypertension-related disease, the pharmaceutical composition comprising: (a) a complex extract of at least five species of herbal medicines selected from the group consisting of Puerariae Radix, Platycodonis Radix, Liriopis Tuber, Dioscoreae Rhizoma, Coicis Semen, and Schisandrae Fructus, as an active ingredient; and (b) a pharmaceutically acceptable carrier.

In an embodiment of the present disclosure, the complex extract as an active ingredient of the composition of the present disclosure comprises any one of the following:

(a) a complex extract of Puerariae Radix, Platycodonis Radix, Dioscoreae Rhizoma, Coicis Semen, and Schisandrae Fructus;

(b) a complex extract of Puerariae Radix, Liriopis Tuber, Dioscoreae Rhizoma, Coicis Semen, and Schisandrae Fructus;

(c) a complex extract of Platycodonis Radix, Liriopis Tuber, Dioscoreae Rhizoma, Coicis Semen, and Schisandrae Fructus; and (d) a complex extract of Puerariae Radix, Platycodonis Radix, Liriopis Tuber, Dioscoreae Rhizoma, Coicis Semen, and Schisandrae Fructus.

Herein, "Puerariae Radix" is the root of *Pueraria lobata* Ohwi or *Pueraria thomsonii* Benth, which is a perennial climbing plant belonging to the family Leguminosae, and indicates the root itself or the root with main bark removed.

Herein, "Platycodonis Radix" is the root of Platycodon *grandiflorum* A. DC., which is a plant of the family Campanulaceae, and indicates the root itself or the root with main bark removed.

Herein, "Liriopis Tuber" is the swollen part of the root of Liriope *platyphylla* Wang et Tang, Liriope *spicata* (Thunb.) Lour, or Ophiopogon *japonicus* Ker-Gawler (the class Liliaceae).

Herein, "Dioscoreae Rhizoma" is the rhizome with main bark removed, of *Dioscorea batatas* Decaisne or *Dioscorea japonica* Thunberg, *Dioscorea* panthaica Prain et Burk, and other species of the same genus (the class Dioscoreaceae), and indicates the rhizome itself or the rhizome that has been steamed and dried.

Herein, "Coicis Semen" is the well ripe seed of *Coix lacryma-jobi* var. ma-yuen (Rom.Caill.) Stapf (the class Gramineae).

Herein, "Schisandrae Fructus" is the well ripe fruit of Schisandra *chinensis* (Turcz.) Baillon or Schisandra sphenanthera Rehd. et Wils (the class Schisandraceae).

The composition of the present disclosure comprises, as an active ingredient, a complex extract of at least five species of herbal medicines selected from the group consisting of Puerariae Radix, Platycodonis Radix, Liriopis Tuber, Dioscoreae Rhizoma, Coicis Semen, and Schisandrae Fructus.

Extracts of the herbal medicines used herein may be purchased or may be obtained by direct extraction from the herbal medicines. The extraction may be performed after each herbal medicine is cut or pulverized into proper sizes.

The complex herbal medicine extract of the present disclosure may be prepared by (i) a single extraction process in which a mixture of at least five species of herbal medicines is subjected to extraction with an extraction solvent or (ii) a method in which extracts of respective single components are separately prepared and then the extracts of the respective components are mixed.

When the extracts used in the composition of the present disclosure are obtained by direct extraction from the respective herbal medicines, various extraction solvents, such as a polar solvent or a non-polar solvent, may be used.

Appropriate examples of the polar solvent include (i) water, (ii) a C1 to C6 lower alcohol (specifically, methanol, ethanol, propanol, butanol, n-propanol, iso-propanol, n-butanol, 1-pentanol, 2-butoxyethanol, or ethylene glycol), (iii) acetic acid, (iv) dimethyl-formamide (DMFO), and (v) dimethyl sulfoxide (DMSO). Appropriate examples of the non-polar solvent include acetone, acetonitrile, ethyl acetate, methyl acetate, fluoroalkanes, pentane, hexane, 2,2,4-trimethyl pentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethyl amine, ethers, carbon tetrachloride, and tetrahydrofuran (THF).

In an embodiment of the present disclosure, the extracts of the present disclosure are extracts from polar organic solvents. As used herein, the term "polar organic solvent" encompasses (a) water, (b) a C1-C4 anhydrous or hydrous lower alcohol (e.g., methanol, ethanol, propanol, butanol, n-propanol, iso-propanol, n-butanol, etc.), and (c) acetic acid, or a mixture of the polar organic solvents.

In an embodiment of the present disclosure, the polar organic solvent of the present disclosure is water, a C1-C4 anhydrous or hydrous lower alcohol, acetic acid, or a mixture of two or more selected from the above-described components.

In an embodiment of the present disclosure, the C1-C4 anhydrous or hydrous lower alcohol of the present disclosure is at least one selected from the group consisting of methanol, ethanol, propanol, butanol, n-propanol, iso-propanol, and n-butanol.

The concentration of the organic solvent may be 1 to 100% (v/v), specifically 10 to 100% (v/v), 20 to 100% (v/v), 30 to 100% (v/v)), 40 to 100% (v/v), 50 to 100% (v/v), 60 to 100% (v/v), 70 to 100% (v/v), 80 to 100% (v/v), and more specifically, 25% (v/v), 30% (v/v), 40% (v/v), 50% (v/v), 60% (v/v), 70% (v/v), 75% (v/v), 80% (v/v), or 90% (v/v), but is not limited thereto.

To prepare the extracts according to an embodiment of the present disclosure, the amounts of solvents used in extraction may be appropriately selected according to the amounts of the herbal medicine components used. Specifically, for example, the amount of a solvent may be a volume corresponding to 1-20 times, more specifically, 2-20 times, 5-15 times, 7-12 times, or 10 times the weight of an herbal medicine, but is not limited thereto.

The extraction temperatures for the extracts of the present disclosure are not particularly limited and may be for example 0° C. to 120° C., and specifically, 15° C. to 95° C.

In an embodiment of the present disclosure, the extraction temperature is preferably 80° C. or higher when the extraction solvent is water, and the extraction temperature is preferably 15° C. to 30° C. when the extraction solvent is a C1-C4 lower alcohol.

The extraction time for the extracts of the present disclosure is not particularly limited, and the extraction time may be for example 1 hour to 10 days or 1 to 120 hours, and specifically, 1 to 72 hours, 1 to 48 hours, 1 to 36 hours, 1 to 24 hours, 1 to 12 hours, 1 to 10 hours, 1 to 6 hours, 6 to 120 hours, 6 to 72 hours, 6 to 48 hours, 6 to 36 hours, 6 to 24 hours, 6 to 12 hours, 36 to 120 hours, 48 to 120 hours, or 72 to 120 hours, but is not limited thereto.

The extracts used in the present disclosure may be extracted through hot water extraction, cold immersion extraction, reflux cooling extraction, ultrasonic extraction, or a conventional extraction method known in the art. In an embodiment of the present disclosure, the extracts of the present disclosure may be prepared through hot water extraction or cold immersion extraction using a lower alcohol, and may be repeatedly extracted 1 to 10 times.

In the present disclosure, the extracts of Puerariae Radix, Platycodonis Radix, Liriopis Tuber, Dioscoreae Rhizoma, Coicis Semen, and Schisandrae Fructus may be used in the form of a crude extract extracted by a solvent, and may be used after high-purity purification.

As used herein, the term "extract" has a meaning that is commonly used as a crude extract in the art as described above but, broadly, encompasses a fraction obtained by additionally fractionating the extract. In other words, the extracts of Puerariae Radix, Platycodonis Radix, Liriopis Tuber, Dioscoreae Rhizoma, Coicis Semen, and Schisandrae Fructus include extracts obtained by using the above-described extraction solvents as well as extracts obtained by additionally applying purification to the same. For example, fractions obtained by passing the extracts through an ultra-filtration membrane with a predetermined molecular weight cut-off value or fractions obtained by additionally performing various purification methods, such as various types of chromatography (designed for separation according to size, charge, hydrophobicity, or hydrophilicity) are also included in the extracts of the present disclosure.

The complex herbal medicine extract of at least five species selected from the group consisting of Puerariae Radix, Platycodonis Radix, Liriopis Tuber, Dioscoreae Rhizoma, Coicis Semen, and Schisandrae Fructus of the present disclosure may be prepared in a powder form by additional procedures, such as distillation under reduced pressure and freeze-drying or spray drying.

In an embodiment of the present disclosure, the mixing weight ratio (w/w) of the effective components Puerariae Radix, Platycodonis Radix, Liriopis Tuber, Dioscoreae Rhizoma, Coicis Semen, and Schisandrae Fructus may be 1-10:1-10:1-10:1-10:1-10:1-10, 1-5:1-5:1-5:1-5:1-5:1-5, 1-3:1-3:1-3:1-3:1-3:1-3, or 1-2:1-2:1-2:1-2:1-2:1-2, and more specifically, 2:1-10:1-10:1-10:1-10:1-10, 1-10:2:1-10:1-10:1-10:1-10, 1-10:1-10:2:1-10:1-10:1-10, 2:2:1-10:1-10:1-10:1-10, 2:1-10:2:1-10:1-10:1-10, 1-10:2:2:1-10:1-10:1-10, 2:1-5:1-5:1-5:1-5:1-5, 1-5:2:1-5:1-5:1-5:1-5, 1-5:1-5:2:1-5:1-5:1-5, 2:2:1-5:1-5:1-5:1-5, 2:1-5:2:1-5:1-5:1-5, 1-5:2:2:1-5:1-5:1-5, 2:1-5:1-5:1-5:1-5, 2:1-3:1-3:1-3:1-3:1-3, 1-3:2:1-3:1-3:1-3:1-3, 1-3:1-3:2:1-3:1-3:1-3, 2:2:1-3:1-3:1-3:1-3, 2:1-3:2:1-3:1-3:1-3, 1-3:2:2:1-3:1-3:1-3, 2:1-2:1-2:1-2:1-2:1-2, 1-2:2:1-2:1-2:1-2:1-2, 1-2:1-2:2:1-2:1-2:1-2, 2:2:1-2:1-2:1-2:1-2, 2:1-2:2:1-2:1-2:1-2, 1-2:2:2:1-2:1-2:1-2, 1-10:1-10:1-10:1:1:1, 1-5:1-5:1-5:1:1:1, 1-3:1-3:1-3:1:1:1, 1-2:1-2:1-2:1:1:1, 2:1-5:1-5:1:1:1, 1-5:2:1-5:1:1:1, 1-5:1-5:2:1:1:1, 2:1-3:1-3:1:1:1, 1-3:2:1-3:1:1:1, 1-3:1-3:2:1:1:1, 2:2:1-3:1:1:1, 1-3:2:2:1:1:1, or 2:1-3:2:1:1:1, and most specifically, 2:2:2:1:1:1, but is not limited thereto.

When one component is excluded in the complex herbal medicine extract, the mixing weight ratio may be applied in the same manner except that only the weight part corresponding to the excluded component is excluded. For example, in a most specific example of 2:2:2:1:1:1, the mixing weight ratio of Platycodonis Radix, Liriopis Tuber, Dioscoreae Rhizoma, Coicis Semen, and Schisandrae Fructus is 2:2:1:1:1 when Puerariae Radix is excluded.

As used herein, the term "mixing weight ratio (w/w)" refers to a weight ratio of respective components before an extraction process. For example, when the complex extract of the present disclosure is prepared through a single extraction process in which a mixture of Puerariae Radix and Platycodonis Radix is subjected to extraction with an extraction solvent, the term indicates a weight ratio of the respective herbal medicines contained in the mixture. When the complex extract of the present disclosure is prepared in a manner in which extracts of herbal medicines as single components are separately prepared and then are mixed, the "mixing weight ratio" indicates a weight ratio of "single component basis weights", each of which is calculated by the following equation:

$$\text{Single component basis weight} = \text{weight of single component used in preparation of single extract} \times (\text{weight of single extract used in preparation of final complex extract/weight of prepared single extract}). \quad \text{[Equation]}$$

The composition of the present disclosure may be prepared into a pharmaceutical composition.

As used herein, the term "prevention" refers to all kinds of actions that inhibit or delays of the development of hypertension or a hypertension-related disease by administration of a composition comprising as an active ingredient the complex herbal medicine extract of the present disclosure.

As used herein, the term "treatment" refers to all kinds of actions that alleviates or advantageously changes symptoms of hypertension or a hypertension-related disease by administration of a composition comprising as an active ingredient the complex herbal medicine extract of the present disclosure.

The pharmaceutical composition of the present disclosure contains a pharmaceutically effective amount of the complex extract. The term "pharmaceutically effective amount" refers to an amount that is sufficient to attain efficacy or activity of the above-described complex extract, and is not particularly limited as long as the purposes of the present disclosure are achieved.

The pharmaceutical composition of the present disclosure comprises a pharmaceutically acceptable carrier. The pharmaceutically acceptable carrier contained in the pharmaceutical composition of the present disclosure is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, water, syrup, and a mineral oil. The pharmaceutical composition of the present disclosure may further comprise, in addition to the aforementioned ingredients, a lubricant, a wetting agent, a sweetening agent, a flavoring agent, an emulsifier, a suspending agent, a preservative, and the like. Suitable pharmaceutically acceptable carriers and preparations are described in detail in Remington's Pharmaceutical Sciences (19th ed., 1995).

An appropriate dose of the pharmaceutical composition of the present disclosure may be variously prescribed according to factors, such as a method for formulation, a manner of administration, patient's age, body weight, sex, and morbidity, food, time of administration, a route of administration, an excretion rate, and response sensitivity. A general dose of the pharmaceutical composition of the present disclosure is in a range of 0.001-1,000 mg/kg in adults. The dose in the human body can be converted based on animal experiments.

The pharmaceutical composition of the present disclosure may be formulated by using pharmaceutically acceptable carriers and/or excipients according to a method that can be easily performed by a person skilled in the art to which the present disclosure pertains, and the pharmaceutical composition may be provided as a unit dosage form or may be packed in a multi-dose container. The formulation may be a solution, suspension, syrup, or emulsion in oil or aqueous media, an extract, a powder, granules, a tablet, or a capsule, and may further contain a dispersant or a stabilizer.

In an embodiment of the present disclosure, hypertension is essential hypertension or secondary hypertension.

In another embodiment of the present disclosure, the hypertension-related disease (or blood pressure disorder-related disease) is postmenopausal hypertension (blood pressure disorder in postmenopausal women), pulmonary arterial hypertension (PAH), stroke, dementia, erectile dysfunction, coronary artery disease, renal failure, myocardial infarction, arrhythmia, vascular aneurysm, heart failure, hypertensive retinopathy, aortic dissection, angina, and pregnancy induced hypertension, but is not limited thereto.

As validated in the examples below, the complex extract of at least five species of herbal medicines selected from the group consisting of Puerariae Radix, Platycodonis Radix, Liriopis Tuber, Dioscoreae Rhizoma, Coicis Semen, and Schisandrae Fructus of the present disclosure significantly reduced the increase in blood pressure compared with a negative control (induced group) and single extract treatment groups with each of Puerariae Radix, Platycodonis Radix, Liriopis Tuber, Dioscoreae Rhizoma, Coicis Semen, and Schisandrae Fructus in the L-NAME-induced hypertension mouse model, and thus the complex extract was identified to have hypertension treatment and alleviation effects.

It was also identified that the complex extract of five species of herbal medicines excluding one component among Puerariae Radix, Platycodonis Radix, Liriopis Tuber, Dioscoreae Rhizoma, Coicis Semen, and Schisandrae Fructus significantly reduced the increase in blood pressure compared with a negative control (an induced group) and each single extract treatment group in the L-NAME-induced hypertension mouse model, and thus the complex extract had hypertension treatment and alleviation effects.

The effects of the complex extract of at least five species of herbal medicines selected from the group consisting of Puerariae Radix, Platycodonis Radix, Liriopis Tuber, Dioscoreae Rhizoma, Coicis Semen, and Schisandrae Fructus showed a synergistic effect on each index compared with individual extracts of Puerariae Radix and Platycodonis Radix.

In accordance with another aspect of the present disclosure, there is provided a food composition for preventing or alleviating hypertension or a hypertension-related disease, the food composition comprising, as an active ingredient, a complex extract of at least five species of herbal medicines selected from the group consisting of Puerariae Radix, Platycodonis Radix, Liriopis Tuber, Dioscoreae Rhizoma, Coicis Semen, and Schisandrae Fructus.

In an embodiment of the present disclosure, the complex extract comprises any one of the following:

(a) a complex extract of Puerariae Radix, Platycodonis Radix, Liriopis Tuber, Dioscoreae Rhizoma, and Coicis Semen;

(b) a complex extract of Puerariae Radix, Platycodonis Radix, Liriopis Tuber, Dioscoreae Rhizoma, and Schisandrae Fructus;

(c) a complex extract of Puerariae Radix, Platycodonis Radix, Dioscoreae Rhizoma, Coicis Semen, and Schisandrae Fructus;

(d) a complex extract of Puerariae Radix, Liriopis Tuber, Dioscoreae Rhizoma, Coicis Semen, and Schisandrae Fructus;

(e) a complex extract of Platycodonis Radix, Liriopis Tuber, Dioscoreae Rhizoma, Coicis Semen, and Schisandrae Fructus; and (f) a complex extract of Puerariae Radix, Platycodonis Radix, Liriopis Tuber, Dioscoreae Rhizoma, Coicis Semen, and Schisandrae Fructus.

As used herein, the term "alleviation" refers to all kinds of actions that ameliorate the extent of hypertension or hypertension-related disease by administration of a composition comprising as an active ingredient the complex herbal medicine extract of the present disclosure.

When the composition of the present disclosure is prepared into a food composition, such a food composition contains the ingredients that are usually added in food manufacturing, for example, proteins, carbohydrates, fats, nutrients, seasonings, and flavoring agents. Examples of the carbohydrates are: common saccharides, such as monosaccharides, e.g., glucose and fructose, disaccharides, e.g., maltose, sucrose, and oligosaccharides, and polysaccharides, e.g., dextrin and cyclodextrin; and sugar alcohols, such as xylitol, sorbitol, and erythritol. Natural flavoring agents and synthetic flavoring agents may be used as flavoring agents. For example, when the food composition of the present disclosure is manufactured into a drink, such a drink may further contain citric acid, liquid fructose, sugar, glucose, acetic acid, malic acid, fruit juice, or the like, in addition to the active ingredient of the present disclosure.

The food composition of the present disclosure can employ the above-described complex extract contained in the pharmaceutical composition according to an aspect of the present disclosure, and a description of overlapping contents therebetween is omitted to avoid excessive redundancy of the present specification.

In accordance with another aspect of the present disclosure, there is provided a method for preventing, treating, or alleviating hypertension or a hypertension-related disease, the method comprising administering to a subject the pharmaceutical composition or food composition comprising, as an active ingredient, the complex extract of at least five species of herbal medicines selected from the group consisting of Puerariae Radix, Platycodonis Radix, Liriopis Tuber, Dioscoreae Rhizoma, Coicis Semen, and Schisandrae Fructus of the present disclosure.

The hypertension or hypertension-related disease, which is a target disease of the treatment method or alleviation method of the present disclosure is as defined with respect to a target disease of the pharmaceutical composition or food composition.

As used herein, the term "administration" or "administer" refers to the direct administration of a therapeutically or remedially effective amount of the composition of the present disclosure to a subject (i.e., an object) undergoing a target disease, thereby forming the equivalent amount thereof in the body of the subject.

The term "therapeutically effective amount" of the composition refers to a content of the composition, which is sufficient to provide a therapeutic or prophylactic effect to a subject, to which the composition is to be administered, and thus the term has a meaning encompassing "prophylactically effective amount". As used herein, the term "subject" is a mammal including a human, a mouse, a rat, a guinea pig, a dog, a cat, a horse, a cow, a pig, a monkey, a chimpanzee, a baboon, a rhesus monkey, and the like. Most specifically, the subject of the present disclosure is a human.

Since the method for preventing, alleviating, or treating hypertension or a hypertension-related disease of the present disclosure corresponds to a method comprising a step of administering the pharmaceutical composition or food composition according to an aspect of the present disclosure, a description of overlapping contents therebetween is omitted to avoid excessive redundancy of the present specification.

Advantageous Effects of Invention

Features and advantages of the present disclosure are summarized as follows.

(a) The present disclosure provides a pharmaceutical composition, comprising a complex herbal medicine extract, for preventing or treating hypertension or a hypertension-related disease.

(b) The present disclosure provides a food composition, comprising a complex herbal medicine extract, for preventing or alleviating hypertension or a hypertension-related disease.

(c) The present disclosure provides a method, for preventing, alleviating, or treating hypertension or a hypertension-related disease, the method comprising administering the complex herbal medicine extract to a subject.

(d) The use of the pharmaceutical composition or food composition of the present disclosure can prevent, alleviate, or treat hypertension or hypertension-related diseases.

DETAILED DESCRIPTION

Hereinafter, the present disclosure will be described in more detail with reference to exemplary embodiments. These exemplary embodiments are provided only for the purpose of illustrating the present disclosure in more detail, and therefore, according to the purpose of the present disclosure, it would be apparent to a person skilled in the art that these examples are not construed to limit the scope of the present disclosure.

EXAMPLES

Preparation Example 1: Preparation of Composite Herbal Medicine Extract Through Extraction with Aqueous Ethanol Solution After washed and dried Puerariae Radix, Platycodonis Radix, Liriopis Tuber, Dioscoreae Rhizoma, Coicis Semen, and Schisandrae Fructus were mixed at a weight ratio (w/w) of 2:2:2:1:1:1, a 70% aqueous ethanol solution (L) corresponding to 10 times the weight (kg) of the mixture was added thereto, followed by extraction with favorable stirring at 20° C. for 72 hours. The extract was filtered, concentrated under reduced pressure at 45-50° C., and then freeze-dried, to thereby obtain a complex herbal medicine extract powder. The yield thereof is shown in Table 1.

TABLE 1

| Classification | Kind of herbal medicine | Yield (%) |
|---|---|---|
| Preparation Example 1-1 | Puerariae Radix, Platycodonis Radix, Liriopis Tuber, Dioscoreae Rhizoma, Coicis Semen, and Schisandrae Fructus (2:2:2:1:1:1) | 19.08 |

Comparative Example 1: Preparation of Single Herbal Medicine Extracts

As for each of washed and dried Puerariae Radix, Platycodonis Radix, Liriopis Tuber, Dioscoreae Rhizoma, Coicis Semen, and Schisandrae Fructus, a 70% aqueous ethanol solution (L) corresponding to 10 times the weight of each herbal medicine was added thereto, followed by extraction with favorable stirring at 20° C. for 72 hours. Each herbal medicine extract was filtered, concentrated under reduced pressure at 45-50° C., and then freeze-dried, to thereby obtain a total of six single herbal medicine extract powders. The yields thereof are shown in Table 2.

TABLE 2

| Classification | Kind of herbal medicine | Yield (%) |
|---|---|---|
| Comparative Example 1-1 | Puerariae Radix | 18.80 |
| Comparative Example 1-2 | Platycodonis Radix | 18.85 |
| Comparative Example 1-3 | Liriopis Tuber | 26.49 |
| Comparative Example 1-4 | Dioscoreae Rhizoma | 12.37 |
| Comparative Example 1-5 | Coicis Semen | 2.36 |
| Comparative Example 1-6 | Schisandrae Fructus | 32.90 |

Comparative Example 2: Preparation of Extracts of Complex Herbal Medicines Extracts Excluding One Species of Herbal Medicine After mixtures of five species of herbal medicines among washed and dried Puerariae Radix, Platycodonis Radix, Liriopis Tuber, Dioscoreae Rhizoma, Coicis Semen, and Schisandrae Fructus were obtained by weight ratios (w/w) shown in Table 3, a 70% aqueous ethanol solution (L) corresponding to of 10 times the weight (kg) of each of the mixtures was added thereto, followed by extraction with favorable stirring at 20° C. for 72 hours. The extracts were filtered, concentrated under reduced pressure at 45-50° C., and then freeze-dried, to thereby obtain a total of six complex herbal medicine extract powders. The yields thereof are shown in Table 3.

TABLE 3

| Classification | Puerariae Radix | Platycodonis Radix | Liriopis Tuber | Dioscoreae Rhizoma | Coicis Semen | Schisandrae Fructus | Yield (%) |
|---|---|---|---|---|---|---|---|
| Comparative Example 2-1 | 2 | 2 | 2 | 1 | 1 | — | 19.54 |
| Comparative Example 2-2 | 2 | 2 | 2 | 1 | — | 1 | 23.33 |
| Comparative Example 2-3 | 2 | 2 | 2 | — | 1 | 1 | 23.22 |

TABLE 3-continued

| Classification | Puerariae Radix | Platycodonis Radix | Liriopis Tuber | Dioscoreae Rhizoma | Coicis Semen | Schisandrae Fructus | Yield (%) |
|---|---|---|---|---|---|---|---|
| Comparative Example 2-4 | 2 | 2 | — | 1 | 1 | 1 | 19.98 |
| Comparative Example 2-5 | 2 | — | 2 | 1 | 1 | 1 | 22.16 |
| Comparative Example 2-6 | — | 2 | 2 | 1 | 1 | 1 | 20.93 |

Test Example 1: Comparison of Blood Pressure Increase Inhibitory Effect Between Complex Extract and Single Herbal Medicine Extracts in L-NAME-Induced Mouse Hypertension For comparative evaluation of the blood pressure increase inhibitory effect between the complex extract and the single herbal medicine extracts, N(G)nitroLarginine methyl ester (L-NAME), a nitric oxide synthase (NOS) inhibitor, was used to induce hypertension in mice, and then the blood pressure of the tail was measured.

The hypertension was induced in 8-week-old female ICR mice by providing 1 mg/mL L-NAME dissolved in drinking water, for one week, and during the same period, a complex extract (Preparation Example 1-1) and single extracts (Comparative Examples 1-1, 1-2, 1-3, 1-4, 1-5, and 1-6) were orally administered at a dose of 200 mg/kg daily. Distilled water was administered for a normal group and a negative control (an induced group).

Figure 1:
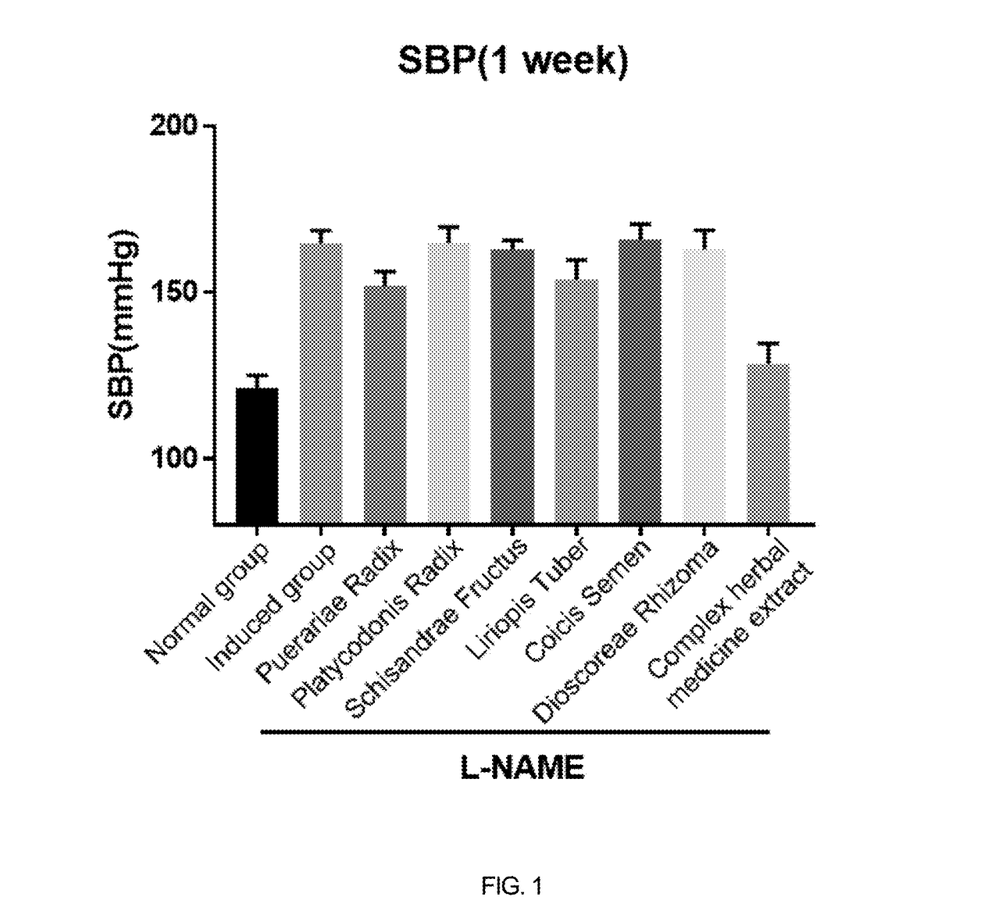
FIG. 1 shows hypertension alleviating effects of single herbal medicine extracts and a complex herbal medicine extract of the present disclosure in the hypertension-induced mouse model according to Test Example 1.

To measure the systolic blood pressure (SBP) of a tail part without anesthesia in mice (n=6-7 per group) that have been administered, a CODA High Throughput Noninvasive Blood Pressure system (CODA, Kent Scientific Co., USA) were used. After a tail cuff was placed on the tail of the mouse, a volume pressure recording (VPR) sensor was installed and the mice were stabilized for 30 to 40 min. Then, an average value of results of 15-20 repeated measurements was used. The results are shown in Table 4 and FIG. 1.

TABLE 4

| Test Group | L-NAME | Test substance | SBP (mmHg) | Blood pressure increase compared with normal group | Blood pressure increase (%) | Activity compared with complex herbal medicine extract, % |
|---|---|---|---|---|---|---|
| Normal group | X | Distilled water | 121.0 ± 4.1 | — | — | — |
| Negative control group (induced group) | ○ | Distilled water | 164.7 ± 3.8 | 43.7 | 100 | — |
| Complex herbal medicine extract (Preparation Example 1-1) | ○ | Preparation Example 1-1 | 128.5 ± 6.2 | 7.5 | 17.0 | 100 |
| Puerariae Radix extract (Comparative Example 1-1) | ○ | Comparative Example 1-1 | 151.8 ± 4.5 | 30.8 | 70.4 | 35.7 |
| Platycodonis Radix extract (Comparative Example 1-2) | ○ | Comparative Example 1-2 | 164.8 ± 4.8 | 43.8 | 100.2 | −0.3 |
| Liriopis Tuber extract (Comparative Example 1-3) | ○ | Comparative Example 1-3 | 153.7 ± 6.0 | 32.7 | 74.8 | 30.3 |
| Dioscoreae Rhizoma extract (Comparative Example 1-4) | ○ | Comparative Example 1-4 | 163.0 ± 5.7 | 42.0 | 96.0 | 4.9 |
| Coicis Semen extract (Comparative Example 1-5) | ○ | Comparative Example 1-5 | 165.9 ± 4.6 | 44.9 | 102.6 | −3.2 |
| Schisandrae Fructus extract (Comparative Example 1-6) | ○ | Comparative Example 1-6 | 163.0 ± 2.6 | 42.0 | 96.0 | 4.9 |

When 1 mg/mL L-NAME was administered through drinking water for one week, the systolic blood pressure increased by 43.7 mmHg compared with the normal group as shown in Table 4. As for the groups receiving the complex extract or single extracts at a dose of 200 mg/kg, the complex herbal medicine extract (Preparation Example 1-1) showed an 83% inhibition of the blood pressure increase, whereas the Puerariae Radix extract (Comparative Example 1-1) showed a 29.6% inhibition, the Liriopis Tuber extract (Comparative Example 1-3) showed a 25.2% inhibition, the Dioscoreae Rhizoma extract (Comparative Example 1-4) and Schisandrae Fructus extract (Comparative Example 1-6)

showed only a 4% inhibition, and the Puerariae Radix extract (Comparative Example 1-2) and Coicis Semen extract (Comparative Example 1-5) showed no effects. Therefore, the complex extract of six species of herbal medicines of Preparation Example 1-1 showed a significantly excellent effect.

Test Example 2: Comparison of Blood Pressure Increase Inhibitory Effect Between Complex Extract and One Herbal Medicine-Excluded Extracts in L-NAME-Induced Mouse Hypertension The hypertension was induced in 8-week-old female ICR mice by providing 1 mg/mL L-NAME dissolved in drinking water for one week, and during the same period, a complex extract (Preparation Example 1-1) and one herbal medicine-excluded extracts (Comparative Examples 2-1, 2-2, 2-3, 2-4, 2-5, and 2-6) were orally administered at a dose of 200 mg/kg daily. Distilled water was administered for a normal group and a negative control (an induced group).

To measure the systolic blood pressure (SBP) of a tail part without anesthesia in mice (n=6-7) that have been administered, a CODA High Throughput Noninvasive Blood Pressure system (CODA, Kent Scientific Co., USA) were used. After a tail cuff was placed on the tail of the mouse, a volume pressure recording (VPR) sensor was installed and the mice were stabilized for 30 to 40 min. Then, an average value of results of 15-20 repeated measurements was used. The results are shown in Table 5 and FIG. 2.

Figure 2:
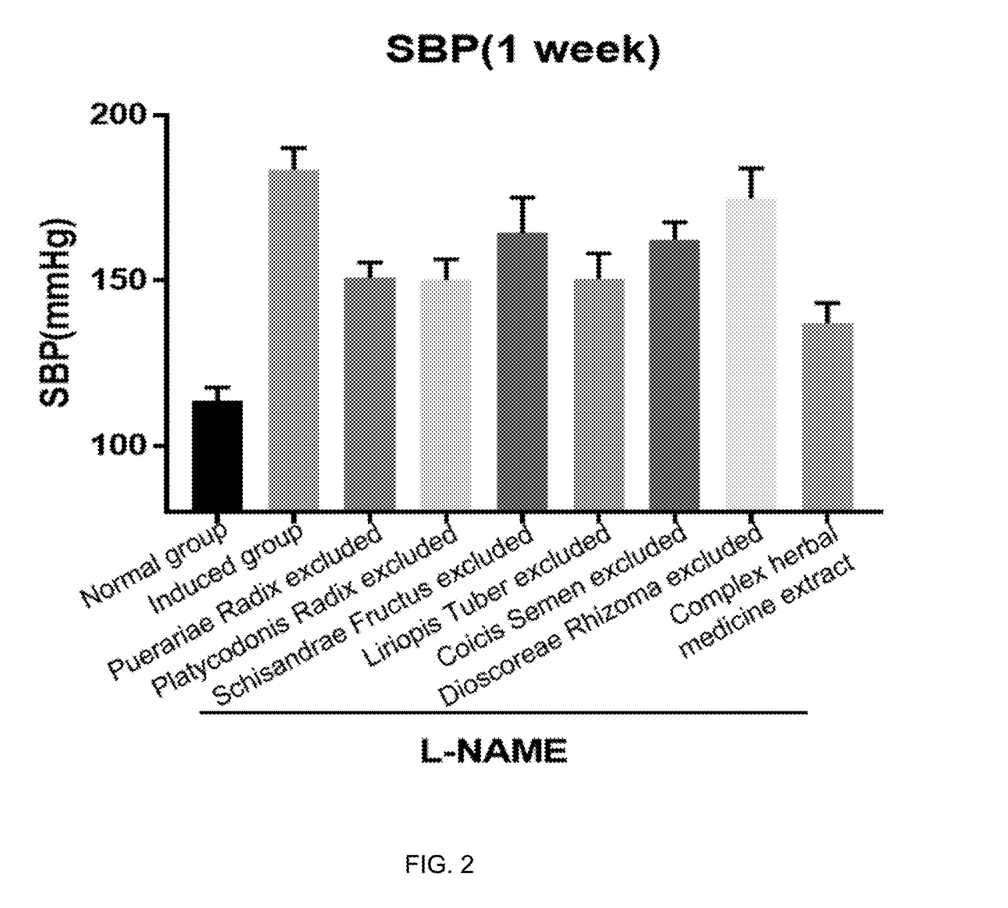
FIG. 2 shows hypertension alleviating effects of complex herbal medicine extracts excluding one species of herbal medicine of the present disclosure in the hypertension-induced mouse model according to Test Example 2.

As shown in Table 5 and FIG. 2, when 1 mg/mL L-NAME was administered through drinking water for one week, the systolic blood pressure increased by 69.7 mmHg compared with the normal group as shown in Table 5. As for the groups receiving 200 mg/kg complex extract or one herbal medicine-excluded extracts, the complex herbal medicine extract (Preparation Example 1-1) showed a 66.6% inhibition of the blood pressure increase, and the Schisandrae Fructus-excluded extract (Comparative Example 2-1) showed a 27.4% inhibition, the Coicis Semen-excluded extract (Comparative Example 2-2) showed a 30.2% inhibition, the Liriopis Tuber-excluded extract (Comparative Example 2-4) showed a 47.3% inhibition, the Platycodonis Radix-excluded extract (Comparative Example 2-5) showed a 47.7% inhibition, and the Puerariae Radix-excluded extract (Comparative Example 2-6) showed a 46.8% inhibition, showing excellent effects. However, the Dioscoreae Rhizoma-excluded extract (Comparative Example 2-3) showed only a 12.4% inhibition.

The blood pressure increase inhibition rates (blood pressure increase inhibitory activities) of the single herbal medicine extracts and the complex extracts of five and six species of herbal medicines in Tables 4 and 5 were compared with the blood pressure increase inhibition rate (100%) of the complex extracts of six species of herbal medicines of Preparation Example 1-1. As a result, the Puerariae Radix extract had the highest activity among the single herbal medicine extracts in Table 4, and all the complex extracts of

TABLE 5

| Test Group | L-NAME | Test substance | SBP (mmHg) | Blood pressure increase compared with normal group | Blood pressure increase (%) | Activity compared with complex herbal medicine extract, % |
| --- | --- | --- | --- | --- | --- | --- |
| Normal group | X | Distilled water | 113.7 ± 4.1 | — | — | — |
| Negative control group (induced group) | ○ | Distilled water | 183.4 ± 6.6 | 69.7 | 100.0 | — |
| Complex herbal medicine extract (Preparation Example 1-1) | ○ | Preparation Example 1-1 | 137.0 ± 6.3 | 23.3 | 33.4 | 100 |
| Schisandrae Fructus excluded (Preparation Example 2-1) | ○ | Comparative Example 2-1 | 164.3 ± 10.8 | 50.6 | 72.6 | 41.1 |
| Coicis Semen excluded (Preparation Example 2-2) | ○ | Comparative Example 2-2 | 162.4 ± 5.2 | 48.7 | 69.8 | 45.3 |
| Dioscoreae Rhizoma-excluded (Preparation Example 2-3) | ○ | Comparative Example 2-3 | 174.8 ± 9.1 | 61.1 | 87.6 | 18.7 |
| Liriopis Tuber excluded (Preparation Example 2-4) | ○ | Comparative Example 2-4 | 150.5 ± 7.8 | 36.8 | 52.7 | 71.0 |
| Platycodonis Radix excluded (Preparation Example 2-5) | ○ | Comparative Example 2-5 | 150.2 ± 6.3 | 36.5 | 52.3 | 71.7 |
| Puerariae Radix excluded (Preparation Example 2-6) | ○ | Comparative Example 2-6 | 150.8 ± 4.7 | 37.1 | 53.2 | 70.3 | five and six species of herbal medicines except for the Dioscoreae Rhizoma-excluded extract (Comparative Example 2-3) in Table 5 had higher activity than the activity (35.7%) of the Puerariae Radix extract compared with the complex extract of six herbal medicines.

It was identified from the above results that the complex extracts of five species of herbal medicines excluding Dioscoreae Rhizoma-excluded extract (Comparative Examples 2-1, 2-2, 2-4, and 2-6) and the complex extract of six species of herbal medicines (Preparation Example 1-1) of the present disclosure were considered to have an excellent synergistic effect compared with the single herbal medicine extracts, and especially, the complex extracts of six species of herbal medicines showed a significantly excellent blood pressure increase inhibitory effect.

What is claimed is:

1. A method for prevention, alleviation, or treatment of hypertension or a hypertension-related disease comprising:
administering a composition to a subject in need thereof, the composition comprising a complex extract of Puerariae Radix, Platycodonis Radix, Liriopis Tuber, Dioscoreae Rhizoma, Coicis Semen, and Schisandrae Fructus, wherein the mixing weight ratio of Puerariae Radix, Platycodonis Radix, Liriopis Tuber, Dioscoreae Rhizoma, Coicis Semen, and Schisandrae Fructus in the complex extract is 2:2:2:1:1:1.

2. The method of claim 1, wherein the extract is an extract with a polar organic solvent.

3. The method of claim 2, wherein the polar organic solvent is water, a C1-C4 anhydrous or hydrous lower alcohol, acetic acid, or a mixture thereof.

4. The method of claim 1, wherein the hypertension is essential hypertension or secondary hypertension.

5. The method of claim 1, wherein the hypertension-related disease is postmenopausal hypertension, pulmonary arterial hypertension, stroke, dementia, erectile dysfunction, coronary artery disease, renal failure, myocardial infarction, arrhythmias, vascular aneurysm, heart failure, hypertensive retinopathy, aortic dissection, angina, or pregnancy induced hypertension.

* * * * *